United States Patent [19]

Conlon, III et al.

[11] Patent Number: 5,078,996

[45] Date of Patent: Jan. 7, 1992

[54] ACTIVATION OF MACROPHAGE TUMORICIDAL ACTIVITY BY GRANULOCYTE-MACROPHAGE COLONY STIMULATING FACTOR

[75] Inventors: Paul J. Conlon, III; Kenneth H. Grabstein, both of Seattle, Wash.

[73] Assignee: Immunex Corporation, Seattle, Wash.

[21] Appl. No.: 888,995

[22] Filed: Jul. 31, 1986

Related U.S. Application Data

[63] Continuation-in-part of Ser. No. 766,893, Aug. 16, 1985, abandoned.

[51] Int. Cl.$^5$ .................. A61K 45/05; A61K 37/66
[52] U.S. Cl. ............................ 424/85.1; 514/2; 514/8; 514/21; 424/85.8; 424/93; 435/69.5; 435/172.2; 435/172.3; 530/350; 530/351; 530/387; 530/828
[58] Field of Search ............. 435/240, 240.20-240.50, 435/69.5, 172.2, 172.3; 514/8; 424/85, 93, 85.1, 85.8

[56] References Cited

U.S. PATENT DOCUMENTS

| | | | |
|---|---|---|---|
| 4,342,828 | 8/1982 | Takaku et al. | 435/240.2 |
| 4,438,032 | 3/1984 | Golde et al. | 435/240.31 |
| 4,675,291 | 6/1987 | Yamamura et al. | 435/68 |

FOREIGN PATENT DOCUMENTS 8504188  9/1985  PCT Int'l Appl.

OTHER PUBLICATIONS

Binz et al, J. Exp. Med., 147, 63–76, (1978).
Berendt et al, J. Exp. Med., 151, 69, (1980).
Nepom et al, Experentia, 39(3), 235–242, (1983).
Flood et al., J. Exp. Med.; 154, 275–290, (1981).
Flood et al, PNAS, 77(3), 2209–2213, (Apr. 1980).
Stevenson et al, J. Immunol., 130(2), 970, (1983).,
Den Otter, Lymphokines, 3, p. 389, (1981).
Moore et al, Lymplokines, 3, 119, (1981).
Grabstein et al, Science, 232, 506–508, (Apr. 1986).
Nathan et al, J. Exp. Med., 160, 600–605, (1984).
Handman, J. Imm., 122(3), 1134, (1979).
Nelson, in "Phagocytes & Cell. Immunity", (Gadebusch, Ed), CRC Press (1979).
Lang et al, Cell, 51, 675–686, (Nov. 1987).
Adams et al, Ann. Rev. Imm., 2: 283–318, (1984).
Arnaut et al, J. Clin. Invest., 78, 597–60, 1986.
Burgess et al, Blood, 56 (6), 947, (1980).
Lopez et al, J. Immunol., 131(6), (Dec. 1983), pp. 2983–2988.
Clark et al, Science, 236, 1229–1237, (Jun. 1987).
Weishart et al, Nature, 314, 361–364, (Mar. 1985).
Nicola et al, Blood, 54(3), 614, (1979).
Handman et al, J. Immunol., 122(3), 1134–1137, (1979).
Wing et al, J. Clin. Investigation, 69, 270–276, 1982.
Ralph et al, Chem. Abs., 98:158918p, 1983.
Meltzer, Lymphokines, vol. 3, pp. 319–343, 1981.
Moore et al, Lymphokines, vol. 3, 119–148, 1981.
Gough et al, Nature, 309, pp. 763–767, Jun. 1984.
Moore et al, J. Immunol., 125(3), 1302–1305, 1980.

(List continued on next page.)

Primary Examiner—Esther L. Kepplinger
Assistant Examiner—Jeff Kushan
Attorney, Agent, or Firm—Jerald A. Nagae; Christopher L. Wight; Scott G. Hallquist

[57] ABSTRACT

Macrophages and precursor monocytes are activated to exhibit tumoricidal activity by stimulation solely with granulocyte-macrophage colony stimulating factor. A patient suffering from tumors can be treated by direct administration of therapeutically effective quantities of activated granulocyte-macrophage colony stimulating factor. Homogeneous granulocyte-macrophage colony stimulating factor for use in activating macrophages and monocyte precursors is prepared by recombinant DNA techniques. The gene coding for granylocyte-macrophage colony stimulating factor is isolated and then recombinant protein product expressed in an appropriate expression system. The granulocyte-macrophage colony stimulating factor recovered from the expression system is purified to homogeneity by reverse phase high-performance liquid chromatography.

26 Claims, 5 Drawing Sheets

OTHER PUBLICATIONS

Cameron et al., "Cytotoxicity of Human Macrophages for Tumor Cells", *J. Clin. Invest.* 63:977 (1979).

Mantovani et al., "Augmentation of Tumoricidal Activity of Human Monocytes and Macrophages by Lumphokines", *Int. J. Cancer* 25:691 (1980).

Kleinerman et al., "Tumoricidal Activity of Human Monocytes Activated In Vitro by Free and Liposome-encapsulated Human Lymphokines", *J. Clin. Invest.* 72:304 (1983).

Roberts and Vasil, *J. Interferon Res.* 2:519 (1982).

Svedersky et al., "Biological and Antigenic Similarities of Murine Interferon and Macrophage-Activating Factor", *J. Exp. Med.* 159:812 (1984).

Onozaki et al., "Role of Interleukin 1 in Promoting Human Monocyte-Mediated Tumor Cytotoxicity", *J. Immunol.*, 135:314 (1985).

Sone et al., "In Vitro Generation of Tumoricidal Properties in Human Alveolar Macrophages Following Interaction with Endotoxin", *Cancer Res.* 42:2227 (1982).

Pick et al., "Intracellular Mediation of Lymphokine Action: Minicry of Migration Inhibitory Factor (MIF) Action by Phorbol Myristate (PMA) and the Ionophore A23187", *Ann. N.Y. Acad. Sci.* 332:378 (1979).

Hand et al., "Requirement for Magnesium Influx in Activation of Alveolar Macrophages Mediated by Ionophore A23187", *Nature (London)* 265:543 (1979).

Schultz et al., *J. Interfon Res.* 2:459 (1982).

```
                  *
                  |  ┌─Sfa NI
                  |  |
CTGCAGCATCTCTGCACCCGCCCGCTCGCCCAGCCCCAGCACACAGCCCTGGGAGCATGTG    61
CysSerIleSerAlaProAlaArgSerProSerProSerThrGlnProTrpGluHisVal
  1           5              10              15

AATGCCATCCAGGAGGCCCGGCGTCTCCTGAACCTGAGTAGAGACACTGCTGCTGAGATG   121
AsnAlaIleGlnGluAlaArgArgLeuLeuAsnLeuSerArgAspThrAlaAlaGluMet
          20              25              30              35

AATGAAACAGTAGAAGTCATCTCAGAAATGTTTGACCTCCAGGAGCCGACCTGCCTACAG   181
AsnGluThrValGluValIleSerGluMetPheAspLeuGlnGluProThrCysLeuGln
          40              45              50              55

ACCCGCCTGGAGCTGTACAAGCAGGGCCTGCGGGGCAGCCTCACCAAGCTCAAGGGCCCC   241
ThrArgLeuGluLeuTyrLysGlnGlyLeuArgGlySerLeuThrLysLeuLysGlyPro
          60              65              70              75

TTGACCATGATGGCCAGCCACTACAAACAGCACTGCCCTCCAACCCCGGAAACTTCCTGT   301
LeuThrMetMetAlaSerHisTyrLysGlnHisCysProProThrProGluThrSerCys
          80              85              90              95

GCAACCCAGATTATCACCTTTGAAAGTTTCAAAGAGAACCTGAAGGACTTTCTGCTTGTC   361
AlaThrGlnIleIleThrPheGluSerPheLysGluAsnLeuLysAspPheLeuLeuVal
         100             105             110             115

ATCCCCTTTGACTGCTGGGAGCCAGTCCAGGAGTGAGACCGGCCAGATGAGGCTGG       397
IleProPheAspCysTrpGluProValGlnGluEnd
         120             125

CCAAGCCGGGGAGCTGCTCTCTCATGAAACAAGAGCTAGAAACTCAGGATGGTCATCTTGG  458

AGGGACCAAGGGGTGGGCCACAGCCATGGTGGGAGTGGCCTGGACTGCCTGGCCACACTGA  519
                              |
                             Nco I

CCTGATACAGGCATGGCAGAAGAATGGGATATTTATACTGACAAATACTGATATTATATAT  580

TATATTTTAAATAATTTAATTTAATTTAATTTAATTGACTAATTACTATTATTACG       641
```

FIG. 1

ACTIVATION OF MACROPHAGE TUMORICIDAL ACTIVITY BY GRANULOCYTE-MACROPHAGE COLONY STIMULATING FACTOR

CROSS-REFERENCE TO RELATED APPLICATION

This is a continuation-in-part of U.S. patent application Ser. No. 766,893, filed Aug. 16, 1985 now abandoned.

TECHNICAL FIELD

The present invention relates to the activation of macrophages, and more particularly, to the activation of macrophages and precursor monocytes to exhibit tumoricidal activity by stimulation solely with granulocyte-macrophage colony stimulating factor (hereinafter "GM-CSF").

BACKGROUND OF THE INVENTION

Macrophages are relatively large (10–20 um), actively motile phagocytic cells that develop from blood-borne monocytes, which in turn originate in the bone marrow. Upon activation, macrophages have been observed to undergo several functional, biochemical and morphological changes, including membrane ruffling, peroxide elaboration, increased expression of Ia antigens and increased secretion of plasminogen. Also, macrophages are considered to be a key element of the immune system. When activated they have been associated with destroying foreign particles and decrepit cells, and also more recently have been identified as providing resistance to and/or eradication of neoplastic disease. The development of activated macrophages and precursor monocytes which display these activities requires the simultaneous presence of effective activation signals and receptive mononuculear phagocytes.

It has been generally accepted that activation of macrophages can be induced by certain lymphokines, referred to as macrophage activating factors or MAF. Cameron et al., *J. Clin. Invest.* 63: 977 (1979); Mantavani et al., *Int. S. Cancer*, 25: 691 (1980); and, Kleinerman et al., *J. Clin. Invest.* 72: 304 (1983).

It is unknown whether MAF is a distint lymphokine or alternatively is in whole or in part composed of other lymphokines. Some researchers have suggested that in the murine system, MAF is composed of gamma interferon ("IFN-$\gamma$"). See Roberts and Vasil, *J. Interferon Res.*, 2: 519 (1982); and, Svedersky et al., *J. Exp. Med.*, 159: 812 (1984).

However, lymphokines other than IFN-$\gamma$ also are thought possibly to activate macrophages to the point where they are capable of killing tumor cells. Macrophages produce the lymphokine interleukin 1 ("IL-1") which is known to stimulate the growth of skin cells, assist in the healing of wounds and cause inflammation and fever. Onozaki et al., *J. Immunol.*, 135: 314 (1985), recently have suggested that IL-1 also promotes tumoricidal activity of fresh monocytes.

It has been reported that macrophages and precursor monocytes also may be activated to display tumoricidal activity by treatment with various reagents, such as the bacterial products lipopolysaccharide ("LPS"), Sone et al., *Cancer Res.*, 42: 2227 (1982), or peptidoglycan or analogs thereof, such as muramyl dipeptide ("MDP"), Nagao et al., *Infec. Immun.*, 24: 304 (1979), Kleiner et al., *Cancer Res.*, 43: 2010 (1983). Other macrophage activating reagents include the tumor promotor phorbol myristate acetate ("PMA"), Pick et al., *Ann. N.Y. Acad. Sci.*, 332: 378 (1979), and ionophores, Pick et al., supra, and Hund et al., *Nature (London)*, 265: 543 (1979).

Recent research reports have indicated that effective activation of macrophages to display nonspecific tumoricidal activity is not the result of a single signal but requires a series of reactions. Meltzer in "Lymphokines," Pick and Landy, eds., Academic Press, New York, pp. 319–343 (1981), postulates that the activation of macrophages to display tumoricidal activity requires the recruitment or accumulation of blood monocytes at a reaction site, such as at an infection, whereat the monocytes differentiate into competent mononuclear phagocytes. After this initial phase of monocyte differentiation, the monocytes are primed into a receptive state by an initial signal derived from a lymphokine. Final maturation of the primed macrophage into cytotoxic activity requires triggering via a second signal derived, for instance, from LPS. When employed in tandem, the concentrations of the priming signal (lymphokine) and triggering signal (LPS) required for a particular level of macrophage activation are much lower than if these signals are used alone, indicating a synergistic cooperation between such signals.

A relationship similar to the lymphokine-LPS cooperation has been reported for LPS and IFN-$\gamma$. Schultz, *J. Interferon Res.*, 2: 459 (1982). The development of recombinant DNA technology combined with in vitro cellular bioassays has lead to the cloning of the cDNAs of IFN-$\gamma$, IL-1 and other lymphokines. The availability of highly pure, recombinant-derived IFN-$\gamma$ has confirmed previous reports of its MAF activity and the requirement of a second triggering signal, such as LPS, to effectively induce IFN-$\gamma$ to display non-specific tumoricidal activity.

The present invention concerns the use of GM-CSF to stimulate macrophages and precursor monocytes to mediate nonspecific tumoricidal activity, which activation is not dependent upon the presence of a costimulator, such as LPS or IFN-$\gamma$. GM-CSF is a particular type of colony stimulating factor ("CSF"). CSF refers to a family of lymphokines that induce progenitor cells found in the bone marrow to differentiate into specific types of mature blood cells. The particular type of mature blood cell that results from a progenitor cell depends upon the type of CSF(s) present. For instance, erythropoietin is believed to cause progenitor cells to mature into erythrocytes while thrombopoietin is thought to drive progenitor cells along the thrombocytic pathway. Similarly, granulocyte-macrophage colony formation is dependent on the presence of GM-CSF. Although the ability of CSF, including GM-CSF, to induce the maturation and proliferation of white cells from bone marrow progenitors is well known, heretofore the capacity of GM-CSF to singularly activate macrophages or precursor monocytes to mediate nonspecific tumoricidal activity has been unknown.

SUMMARY OF THE INVENTION

In accordance with the present invention, macrophages or monocyte precursors are activated to mediate nonspecific tumoricidal activity solely by a GM-CSF signal. The activated macrophages or monocyte precursors may be employed to inactivate tumor cells in vivo or in vitro. Patients suffering from tumors may be treated by isolating macrophages, monocytes or earlier precursors from the patient's body and then stimulating the isolated cells to display tumoricidal activity by culturing the cells with a therapeutically effective quantity of GM-CSF. Thereafter the stimulated cells can be administered to the patient whereupon the activated cells seek out and destroy the tumors inflicting the patient. Alternatively, formulations of GM-CSF can be administered directly to the cancer patient, either by intravenous, subcutaneous, intraperitoneal or intramuscular injection, or by nasal inhalation. It will be appreciated that through the present invention, tumor patients can be treated with activated macrophages without subjecting the patients to endotoxins, radioactive materials or other harmful substances.

Sufficient quantities of homogeneous GM-CSF for use in the present invention may be produced by recombinant DNA techniques. The gene coding for GM-CSF is isolated and then engineered for use in systems capable of high level expression of the recombinant protein. The GM-CSF recovered from expression hosts is purified to homogeneity by use of reverse phase high-performance liquid chromatography.

A procedure for demonstrating the effectiveness of activated macrophages or precursor monocytes in killing particular tumors includes culturing macrophages or monocyte precursors with GM-CSF at various concentrations. After an appropriate culture period, the GM-CSF is removed and then the target tumor cells, after being radiolabeled, are subjected to the activated macrophage effector cells. After a further culture period, the target cells that were killed are removed and then the remaining target cells lysed to measure residual counts as a quantitative index of the number of cells which survived exposure to activated macrophages.

BRIEF DESCRIPTION OF THE DRAWINGS

The details of typical embodiments of the present invention will be described in connection with the accompanying drawings, in which:

FIG. 1 illustrates the nucleotide and corresponding amino acid sequences of the human GM-CSF gene, including the 3' noncoding region;

DESCRIPTION OF THE INVENTION

Preparation of Precursor Monocytes

Figure 2:
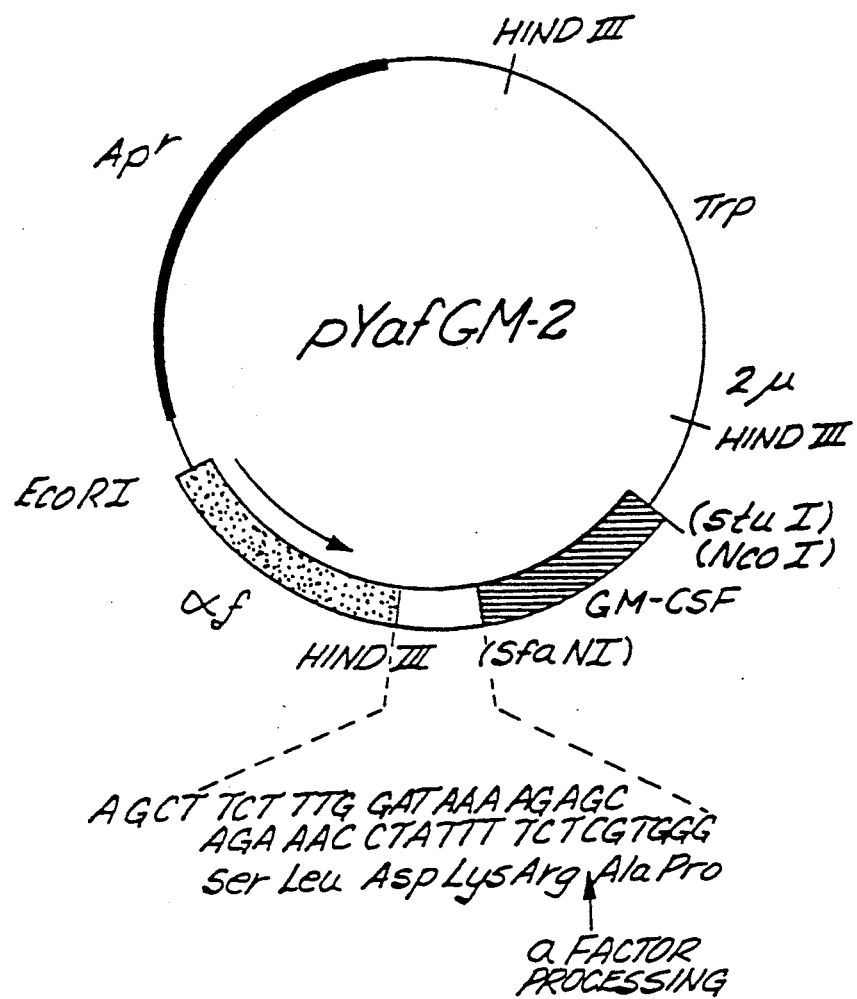
FIG. 2 illustrates the pY fGM-2 expression plasmid with the coding region of the GM-CSF gene inserted therein for use in transforming host cells to express functional human GM-CSF.

Macrophages in the form of peripheral blood monocytes were purified for subsequent activation by GM-CSF using standard techniques including Ficol and Percoll separation. The top monocyte layer resulting from these procedures is plated in medium and then nonadherent cells removed so that the remaining monolayers can be activated by the addition of GM-CSF and other possible activating agents including LPS and IFN-γ. To guard against the presence of contaminants, such as an endotoxin, the reagents used in the cell separation process were tested by Limulus Ameobocyte Lysate. Furthermore, cell populations were prepared with endotoxin free buffers and media.

Rather than being isolated from peripheral blood, monocytes or mature macrophages can be derived from other sources, such as spleen cells, lymph node cells or lung lavages.

Preparation of Recombinant GM-CSF; Cloning of GM-CSF Gene

GM-CSF is produced only in minute quantities in vivo. In accordance with the present invention, relatively large quantities of highly pure GM-CSF for use in activating monocytes and macrophages is produced through recombinant techniques. A discussion of such recombinant DNA techniques for protein production is set forth in the editorial and supporting papers and Vol. 196 of *Science* (April 1977). To take advantage of the recombinant DNA techniques discussed in this reference, the gene coding for GM-CSF must first be isolated from a cDNA library, for instance, with a nick-translated cDNA probe. The labeled probe is derived from a murine GM-CSF cDNA library by use of a synthetic oligonucleotide probe corresponding to the portion of the nucleotide sequence of murine GM-CSF.

To isolate the molecular clone of the human GM-CSF gene, total RNA is extracted from lymphoma cell lines, such as HUT-102, Jurkat or HL60, or from other types of sources, such as human peripheral blood mononuclear cells. Polyadenylated mRNA is isolated from the total RNA extract. A cDNA library is constructed by reverse transcription of the polyadenylated mRNA with the enzyme avian myeloblastosis virus ("AMV") reverse transcriptase. The DNA is rendered double-stranded with DNA polymerase I and inserted into an appropriate cloning vector, such as a plasmid, bacteriophage or cosmid. Resultant recombinant cloning vectors are then used to transform an appropriate host, such as *Escherichia coli* ("*E. coli*"), yeast or other unicellular organism.

Transformed hosts are identified and grouped into pools. Plasmid DNA, prepared from these pools, is hybridized with a nick-translated cDNA murine GM-CSF probe radiolabeled with $^{32}P$. The pool(s) of clones that give a positive signal to the probe is identified and then the putative pool subdivided and hybridization screen repeated. A single transformant corresponding to the human GM-CSF gene is eventually identified. Plasmid DNA is prepared from this transformant and characterized by DNA sequencing using, for instance, standard chain-termination methods as originated by Sanger et al., *Proc. Natl. Acad. Sci. (U.S.A.)*, 70: 5463 (1977).

FIG. 1 illustrates the nucleotide sequence of the human GM-CSF gene. The coding region of the human GM-CSF gene extends from nucleotide No. 14 to nucleotide No. 394. The corresponding amino acid sequence, as determined from the nucleotide sequence, is set forth below the relevant codons. Plasmid DNA, designated as pHG23, prepared from the cDNA of the identified positive colony and transformed into *E. coli* is on deposit with the American Type Culture Collection ("ATCC"), 12301 Parklawn Drive, Rockville, Md. 20852, U.S.A., under Accession No. 39900.

Expression of Functional GM-CSF

Functional GM-CSF is produced by expressing the GM-CSF gene contained in pHG23 in host cells and then tested for the ability of the expressed product to stimulate the growth of bone marrow colonies in agar. A cDNA fragment of substantially the entire coding region of the GM-CSF gene shown in FIG. 1 (the Sfa NI to the Nco I fragment) is inserted into an expression vector designed to direct synthesis and secretion of GM-CSF from yeast host cells, for instance a vector designated as pYαfGM-2 as shown in FIG. 2. The expression vector, such as pYαfGM-2, preferably contains sequences derived from plasmid pBR332 (thick line portion in FIG. 2) including an origin of replication and the ampicillin-resistance gene (Ap$^r$). Ideally, the expression vector also includes sequences from yeast, for instance, the tryptophan-1 gene (TRP-1) as a selectable marker and the 2u yeast origin of replication (thin line portion). The expression vector preferably further includes the yeast pre-pro-α mating factor ("α-factor") (stippled box portion) as an efficient promoter together with leader sequences to direct the synthesis and secretion of GM-CSF in yeast hosts, followed by the sequence for the coding region of GM-CSF shown in FIG. 1 (hatched box portion). The structure of the α-factor gene is discussed in Kurjan and Herskowitz, *Cell*, 30: 933–943 (1982).

The pYαfGM-2 expression plasmid is transformed into an appropriate strain of *Saccharomyces cerevisiae* ("*S. cerevisiae*"). Preferable strains include yeast strain Nos. 79, X2181-1B, DBY746, YNN280, and 20B-12. These strains are all α, Trp I, Leu 2 for compatibility with the α-factor promoter and for selection of Trp+ transformants. These strains are all widely available, for instance strain 79 is available from the Yeast Genetic Stock Center, Department of Biophysics and Medical Physics, University of California, Berkeley, Calif. 94702.

Transformation of the yeast host with the recombinant expression plasmid containing the bIL-2 gene is conducted according to well-known procedures wherein spheroplasts are formed and then washed prior to plasmid uptake. Standard protocols for this procedure have been established. See, for example, Beggs, *Nature (London)*, 275: 104 (1978); and, Hinnen et al., *Proc. Natl. Acad. Sci. (U.S.A.)*, 75: 1929 (1978).

Yeast fermentation supernatants are assayed for biological activity by their ability to direct the formation of mixed, granulocytic and macrophage-type colonies from human bone marrow cells. As a control, plasmid pYαf, of the same construction as pYαfGM-2, but lacking the GM-CSF sequences, was also transformed into a yeast host and the fermentation supernatant tested for biological activity. The pYαfGM-2 supernatant was found to direct synthesis of high levels of GM-CSF activity in the bone marrow assay ($1.2 \times 10^6$ colony forming units per milliliter culture ("CFU-c/ml")) whereas no activity was detected from the supernatant derived from the pYαf control plasmid.

Purification of Recombinant GM-CSF

The recombinant GM-CSF contained in the supernatant of the expression host cells is purified to essential homogeneity by reverse phase high-performance liquid chromatography ("HPLC"). The HPLC procedures used in the present invention preferably employ a reverse phase, tetramethyl, octadecyl, octylmethyl or diphenyl-bonded silica column having a pore size sufficiently large to be optimally utilized with the protein GM-CSF, i.e., a pore size of at least 300 Å.

Suitable reverse phase HPLC columns for use in the practice of the present invention are articles of commerce. A preferable column for this purpose is the Vydac line of columns commercially available from Separations Group, Hesperia, Calif. For example, the present invention may employ the Vydac C4 or C18 adsorbent reverse phase columns consisting of tetramethyl silane groups covalently bonded by means of siloxane (silican-oxygen-silican) bonded to the surface of 300 Å pore diameter silica gel which has been classified to a mean particle size of from 30 to 44 microns.

Prior to being applied to the column, the expressed GM-CSF is rendered acidic with an appropriate acid, such as trifluoroacetic acid ("TFA"). The elution of proteins from the HPLC column is carried out in a manner well known in the art. A suitable elution procedure for removing the bonded proteins from the column involves the use of a linear gradient of acetonitrile. A preferred gradient for this purpose is 0 to 100% (vol/vol) acetonitrile gradient in TFA (pH2.0–2.1).

The eluted protein can be conveniently monitored with detection systems that are well known in the art. For example, the relative protein concentrations in fractions eluted from the HPLC column can be determined by measuring absorbance of the eluted material in an automated ultraviolet light sapectrophotometer, at 214 nanometers light wavelengths. A suitable automated ultraviolet light absorbance detection apparatus is available from Waters Associates, Milford, Me.

Fractions recovered from the HPLC procedure are analyzed for protein by the fluorescamine assay and by SDS (sodium dodecyl sulfate) polyacrylamide gel electrophoresis followed by silver staining, as described in Example 4, infra. The recovered GM-CSF, designated as Fxn 57, is then assayed for biological activity using the bone marrow colony-forming assay discussed above and in Example 3, infra.

Figure 5:
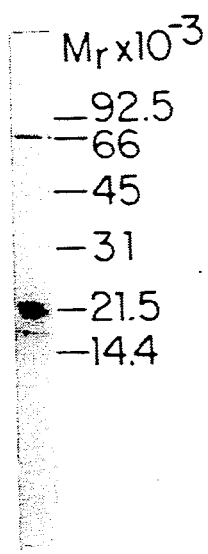

If sufficient protein purification is not achieved by the initial HPLC procedure, it can be repeated by use of the same column or a different type of column. In addition, the same or a different eluant may be employed. By carrying out the HPLC in two steps, the GM-CSF was purified to homogeneity as a single symmetric peak of biological activity. As shown in FIG. 5, by polyacrylamide gel electrophoresis, two bands of GM-CSF activity having molecular weights of about 21,000 and 17,000 daltons were identified. These bands correspond to glycosylated (21,000) and unglycosylated (17,000) species of GM-CSF produced by yeasts. In the bone marrow colony-forming assay the activity level of the Fxn 57 was found to be $1.5 \times 10^7$ CFU-c/ml. The specific activity of this homogeneous GM-CSF was found to be approximately $1.5 \times 10^6$ CFU-c/ug protein, or $3.0 \times 10^{16}$ CFU-c/mole.

Preparation of Target Cells

Activation of monocyte/macrophages into tumoricidal state is assayed with respect to various types of tumor cells, including, for instance, the A375 human myeloma cell line (ATCC No. CRL 1619), the human bladder squamous carcinoma SCaBER (ATCC No. HTB3), the human astrocytoma gliobastomas U-87 MG and U-373 MG (ATCC Nos. HTB 14 and 17, respectively), the human Ewing sarcomas Esa-1 and SK-ES-2 (ATCC Nos. HTB 83 and HTB 87), the human malignant melanomas SK-MEL-28 and SK-MEL-31 (ATCC Nos. HTB 72 and HTB 73), the human liver carcinoma SK-Hep-1 (ATCC No. HTB-52); the human pancreatic carcinoma MIA PACA-2 (ATCC No. CRL-1420) and the human bladder carcinoma 5637 (ATCC No. HTB-9). Prior to assay, the target cells are grown in monolayers in medium supplemented with various additives, such as fetal calf serum ("FCS"). Thereafter, the target cells are radiolabeled, for instance with [$^{125}$I] iododeoxyuridine ("[$^{125}$I] IUdR"). A standard protocol for the labeling procedure is set forth in Kleinerman et al., supra, and, Onozaki, supra.

Assay for Tumoricidal Activity

Various concentrations of test samples of putative activator substances, i.e., GM-CSF, IFN-$\gamma$, LPS are added to the plated monocytes, prepared above. After an appropriate culture period, i.e., 24 hours, the test sample is removed and radiolabeled target cells added to the culture wells. After a further initial incubation period, the culture supernatants are removed and fresh medium replaced. Then after a final culture period, target cells killed by the activated monocytes are removed and the remaining viable cells in each well lysed with an appropriate reagent, such as NaOH. The radioactivity of the lysate is then measured in a gamma counter. Wells which contain radiolabeled target cells, but without activated monocytes, serve as a control for target cell viability.

The cytotoxic activity mediated by the activated monocytes is calculated as follows:

Percentage of spontaneous cytotoxicity = 100 −

$$\frac{\text{cpm in target cells cultured with monocytes}}{\text{cpm in target cells alone}} \times 100$$

Percentage of specific cytotoxicity mediated by activated monocytes = 100 −

$$\frac{\text{cpm in target cells cultured with activated monocytes}}{\text{cpm in target cells cultured with control monocytes}} \times 100$$

Figure 3:
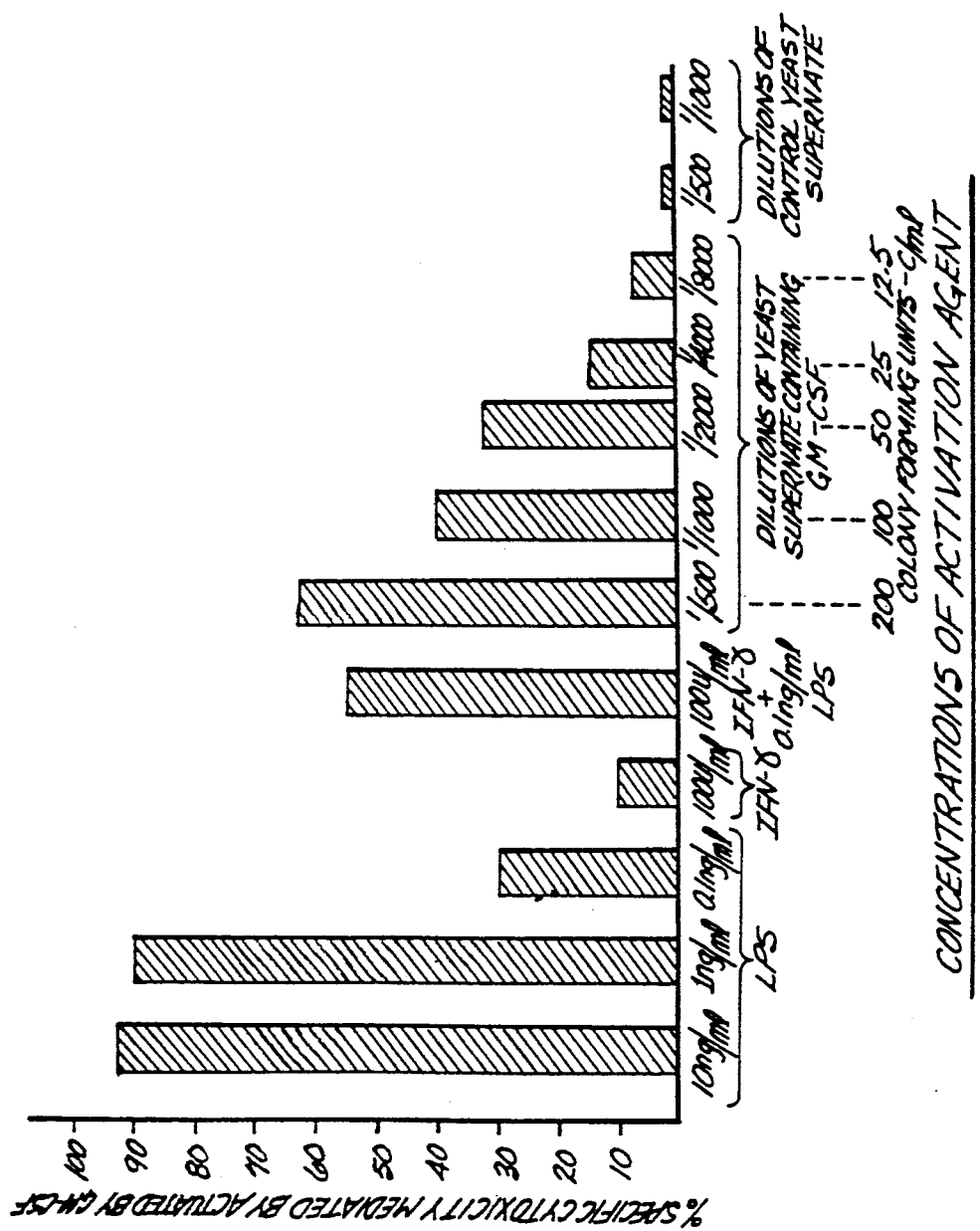
FIG. 3 is a graph illustrating the percent of specific lysis of tumor cells mediated by human peripheral blood macrophages activated by recombinant human GM-CSF.
Figure 4:
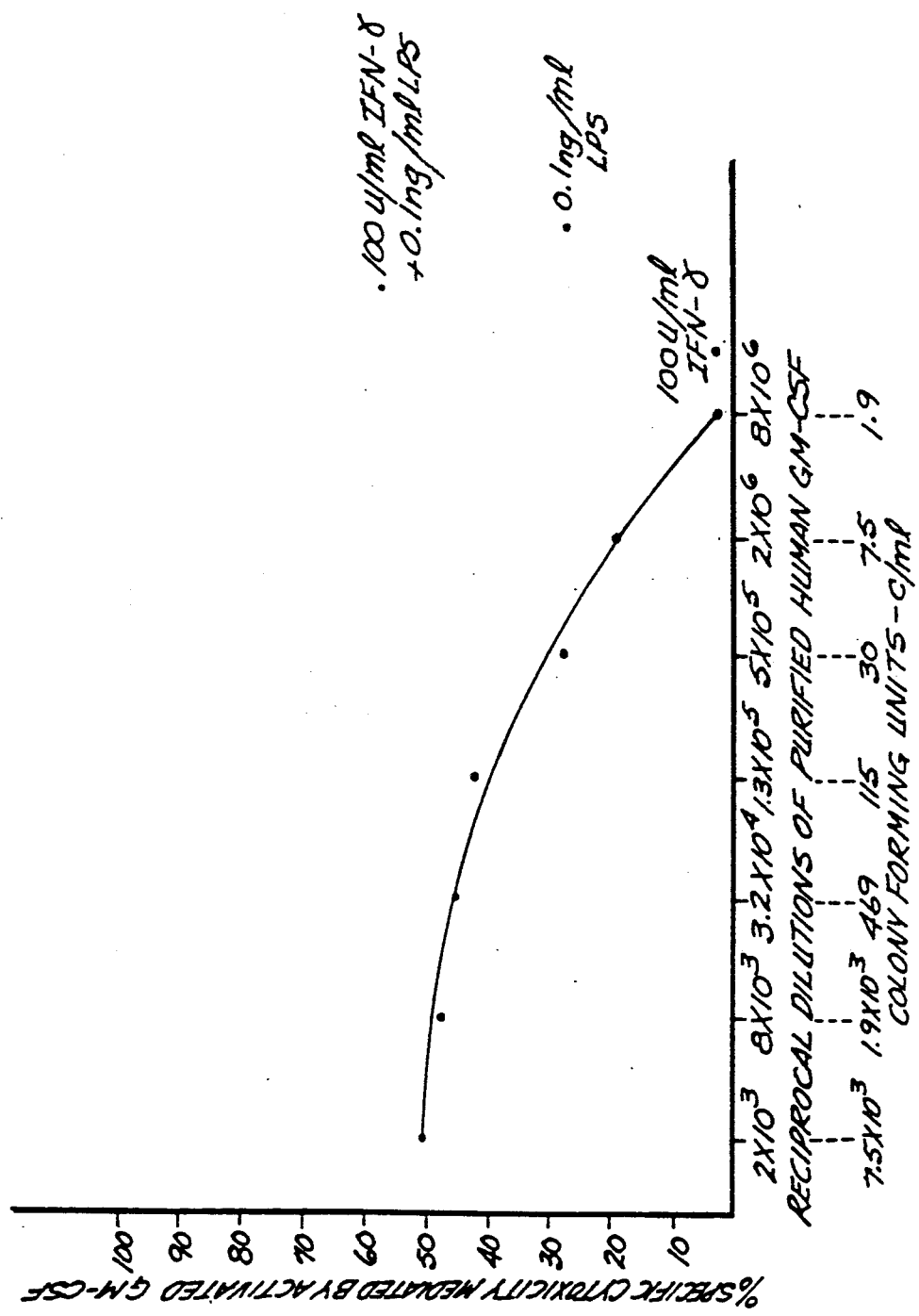
FIG. 4 is a graph illustrating the specific lysis of tumor cells mediated by human peripheral blood macrophages activated by various concentrations of purified recombinant human GM-CSF and comparable lysis mediated by macrophages activated with LPS, IFN-γ and IFN-γ combined with LPS; and, FIG. 5 is a photograph of a silver stained polyacrylamide gel band of purified homogeneous recombinant GM-CSF.

FIGS. 3 and 4 illustrate the tumorcidal activity of human peripheral blood monocytes activated with various concentrations of recombinant human GM-CSF, LPS, IFN-$\gamma$ or LPS together with IFN-$\gamma$. Specifically, FIG. 3 illustrates the dose dependent capacity of LPS and IFN-$\gamma$ individually and combined to induce macrophage-mediated tumor target destruction. FIG. 3 also shows the activity of various concentrations of yeast supernatant containing recombinant GM-CSF. As depicted in FIG. 3, such yeast supernatant at a dilution of 1: 500 (200 CFU-c/ml) stimulated macrophages to generate approximately 65% specific cytotoxicity. As also set forth in FIG. 3, control yeast fermentation supernate was not capable of inducing macrophage cytotoxicity. Crude yeast supernate has a titer of approximately 1-2×10$^5$ CFU-c/ml.

FIG. 4 shows a full course dose response titration of purified recombinant human GM-CSF. As illustrated in FIG. 4, a half-maximal induction of macrophage mediated tumor-cell cytotoxicity occurs at a dilution of the column fraction containing homogeneous GM-CSF of approximately 1: 1,000,000 (15 CFU-c/ml). Control data illustrating the cytotoxicity of IFN-$\gamma$, LPS and LPS combined with IFN-$\gamma$ are also shown in FIG. 4.

As apparent from the foregoing, GM-CSF effectively functioned as a singular signal to induce monocytes to exhibit tumorcidal activity. This is a biologic property of GM-CSF that heretofore has been unknown.

Treatment of Tumor Patients

Purified recombinant GM-CSF as prepared above may be employed to treat patients or other mammals suffering from tumors using various therapy procedures. Therapeutically effective doses of GM-CSF can be administered to a subject in need of treatment by a variety of conventional routes, such as parenterally or transdermally. In general, the recombinant GM-CSF may be administered in dosages of about 1.0 to 10$^6$ ug/kg of body weight of the subject per day. Preferably treatment is initiated at a lower level of this dosage range and then increased until the desired therapeutic effect is achieved. Also, variations in dosage will necessarily occur depending upon various factors, for instance the condition of the subject being treated. The person responsible for administration will, in any event, determine the appropriate dose for the individual subject.

For parenteral administration, the recombinant GM-CSF may be introduced into the subject in single or multiple doses by way of, for example, subcutaneous, intramuscular, intraperitoneal, or intravenous injection. Alternatively, the GM-CSF could be introduced via aerosol inhalation, transdermal or transbuccal absorption or rectal suppository. For administration by injection, solutions of recombinant GM-CSF in sesame oil or peanut oil or aqueous propylene glycol may be employed, as well as sterile nontoxic, nonallergic solutions of distilled water, serum albumin, Ringer's solution, Hank's solution, etc. Such solutions could be suitably buffered if necessary and the liquid diluent first rendered isotonic with sufficient saline or glucose.

As a further treatment protocol, macrophages or precursor cells thereof can be isolated from a donor and stimulated into tumoricidal activity by culturing the cells with a therapeutically effective quantity of GM-CSF. The activated macrophages or precursor cells can then be administered to a recipient using one of the techniques discussed above. Typically, but not in all instances, the donor and recipient are the same individual.

The present treatment procedures may be employed with respect to virtually all types of tumors, especially "solid" tumors. Such tumors include all carcinomas, such as bladder, kidney, squamous cells, lung, liver, breast and colon. Such tumors also include any melanoma or sarcoma.

The processes and products of the present invention are further illustrated by the following examples. The following examples are merely exemplary; they are presented to illustrate the present invention and to assist one of ordinary skill in making and using the same. The examples are not intended to limit in any way the scope of the disclosure, the claims set forth below or the protection granted by Letters Patent herein.

EXAMPLE 1

Preparation of Peripheral Blood Monocytes

The buffy coat portion of peripheral blood monocytes (obtained from Portland, Oreg., Red Cross) was purified using pyrogen-free reagents as measured by Limulus Ameobocyte Lysate (Whittaker M.A. BioProducts, Walkersville, Md). Each buffy coat was diluted in Roswell Park Memorial Institute ("RP MI")-

1640 medium with heparin (50 U/ml, Sigma Chemical Co., St. Louis, Mo.) to 200 ml of cells and layered on Isolymph (Gallard-Schlesinger, Carle Place, N.Y.) and then centrifuged at 1400×g for 25 minutes. The interface cells (mononuclear leucocytes) were washed and then layered, at a concentration of from 4 to 5×10⁷ cells in 2 ml, on continuous Percoll (Pharmacia Fine Chemicals) gradients and then centrifuged at 200×g for 20 minutes at 4° C. to separate the monocytes from the remainder of the mononuclear leukocytes. The resulting top, monocyte layer was collected, washed in RP MI-1640 with 5% FCS and then plated at a concentration of from 1 to 2×10⁵ cells per well in flat-bottomed 96-well Microtiter plates (Costar, Cambridge, Ma.) together with RP MI-1640 and 5% FCS. After incubation for one hour at 37° C., the nonadherent cells were removed by aspiration with an 18 gauge needle and then the monocyte layers rinsed twice with serum free RP MI-1640 medium thereby readying the monocytes for addition of test samples composed of various concentrations of putative activators, such as GM-CSF, IFN-γ, LPS or LPS combined with IFN-γ, as discussed more fully below.

EXAMPLE 2

Preparation of Recombinant GM-CSF

Substantially the entire coding region and a portion of the 3' flanking region of the GM-CSF gene were removed from the cDNA clone of FIG. 1 and employed to form a recombinant expression plasmid, designated as pYafGM-2 to direct GM-CSF expression in yeast host cells. The pYafGM-2 expression plasmid is on deposit with the ATCC under Accession No. 53157. As shown in FIG. 2, pYafGM-2 includes an origin of replication and an Ap^r resistant gene from plasmid pBR322 (thick line portion). The expression plasmid also includes the yeast 2u circle origin of replication and a Trp I gene for selection of transformed yeast hosts (TRP-[Trp-auxotrophs], thin line portion in FIG. 2). The expression plasmid further includes the yeast α-factor promoter and leader sequences (stippled box portion) for use in directing transcription and secretion of GM-CSF. The GM-CSF sequences (hatched box portion) are fused to the α-factor sequences with a synthetic oligonucleotide (open box portion), as discussed more fully below.

As noted above, the coding region of the GM-CSF gene, from the Sfa NI to the Nco I site, was removed from the pHG23 clones by use of Sfa NI and Nco I restriction enzymes in a standard protocol, for instance as set forth in Maniatis et al., *Molecular Cloning, A Laboratory Manual*, Cold Spring Harbor Laboratory, Cold Spring Harbor, N.Y. The Sfa NI enzyme cleaves the GM-CSF gene from the pHG23 clone at a location which is two nucleotides downstream from the 5' terminus of the region coding for the mature protein (nucleotide No. 14), since no restriction site was found to correspond precisely to nucleotide No. 14. An oligonucleotide was chemically synthesized to add back the 5' terminal portion of the coding region of the mature GM-CSF gene and also to add a second α-factor processing site to obtain complete processing of the signal sequence for secretion of the mature form of GM-CSF. The composition of the oligonucleotide, as shown in Table I below, and in FIG. 2 (open box portion), includes a Hind III cohesive 5' terminal, followed by a Cathepsin B-like maturation site composed of the sequence: TCT TTG GAT AAA AGA, followed by a Sfa NI cohesive 3' terminal coding for the first two amino acid residues of the mature GM-CSF protein. Although the oligonucleotide shown in Table I was chemically synthesized by triester technique as detailed by Sood et al., *Nucl. Acad. Res.*, 4:2557 (1977); and, Hirose et al., *Tet. Lett.*, 28:2449 (1978), it is to be understood that the oligonucleotide can be prepared by other methods, such as by the phosphodiester method.

TABLE 1

| 5'— | A | GCT | TCT | TTG | GAT | AAA | AGA | GC  |     | —3' |
|     |   |     | AGA | AAC | CTA | TTT | TCT | CGT | GGG |     |
|     |   |     | Ser | Leu | Asp | Lys | Arg | Ala | Pro |     |

It is to be understood that other standard recombinant DNA techniques could be used to generate the same expression vector, and that the construction detailed above is an illustrative but nonlimiting representative of various strategies that could be used to prepare a GM-CSF cDNA fragment for insertion into the pYafGM-2 expression vector, or for expression in other bacterial or mammalian vectors.

The pYafGM-2 vector was transformed into yeast strain 79 (α, Trp 1-1, Leu 2-1) of *S. cerevisiae* for selection of Trp⁺ transformants by standard techniques. Prior to transformation, the strain 79 was grown either in selective media (YNB-trp, consisting of 0.67% Yeast Nitrogen Base (Difco Labs, Detroit, Mich.), 0.5% (Casamino acids, 2% glucose, 10 micrograms/milliliter ("ug/ml") adenine and 20 ug/ml uracil); or, in rich media (YPD, consisting of 1% yeast extract, 2% peptone and 2% glucose supplemented with 80 ug/ml adenine and 80 ug/ml uracil). Cells were harvested by centrifugation at 1000×g for 5 minutes at 22° C., and then the resulting pellet was washed with sterile, distilled water.

The yeast cells were then concentrated by resuspending in 1/10 vol. of SED (1M sorbitol, 25 mM ethylene diamine tetracetate ("EDTA") [pH 8.0], and 50 mM dithiothreitol) and incubating for 10 minutes at 30° C. The cell-buffer mixture was then centrifuged for 5 minutes at 300×g. The pellet was washed once with 1/10 vol. of 1M sorbitol and the cells resuspended in 20 milliliters of SCE (1M sorbitol, 0.1M sodium citrate [pH 5.8], 0.01M EDTA). Glusulase, to break down the cell walls, in an amount of 10⁻³ vol. was added to the solution and then the solution was incubated at 30° C. for 30 minutes with occasional gentle shaking. The presence of spheroplasts was assayed by diluting 10 microliters ("ul") of the yeast cells into a drop of 5% SDS (wt./vol.) on a microscope slide to observe for "ghosts" at 400×phase contrast. The cell mixture was then centrifuged at 300×g for 3 minutes. The resulting pellet was twice washed with 1/10 vol. of 1M sorbitol and then once with CaS (1M sorbitol, 10 mM CaCl₂).

Next, the yeast spheroplasts were transformed with the previously prepared plasmid vector in a procedure adapted from Beggs, supra. The pelleted spheroplasts were suspended in 1/200 vol. of CaS and divided into 100 microliter aliquots in 1.5 ml Eppendorf tubes. From 1 to 10 ul of the plasmid DNA were added to each aliquot (0.5 to 5 ug). The mixture was incubated at room temperature for 10 minutes and then 1 ml of PEG (20% PEG 4000, 10 mM $CaCl_2$, 10 mM Tris-HCl [pH 7.4]) was added to each aliquot to promote DNA uptake. After 10 minutes at room temperature, the mixture was centrifuged for 5 minutes at 350×g. The resulting pellet was resuspended in 150 ul of SOS (10 ml of 2M sorbitol, 6.7 ml of YEPD [1% (wt/vol) yeast extract, 2% (wt/vol) peptone, 2% (wt/vol) glucose], 0.13 ml of 1M $CaCl_2$, 27 ul of 1% tryptophan and 3.7 ml of water). This mixture was incubated for 20 minutes at 30° C. The cells were then plated.

Prior to plating, the protoplast/DNA mixture selective plates were preincubated at 37° C. Three ml of melted top agar (45° C.), composed of 18.2 ml of sorbitol, 2 gm agar, 0.6 gm Difco yeast nitrogen base (without amino acids), 2 gm glucose, 0.1 ml of 1% adenine, 0.4 ml of 1% uracil and amino acids as required, was then added to each aliquot of transformed cells and the tube contents poured on the selective plates. The plates were incubated from 2 to 4 days at 30° C. Colonies which developed in the Trp minus medium contained plasmids that have the Trp 1 gene, i.e., those that are transformed.

Prior to biological and tumoricidal assays, the transformants were grown in 20-50 ml of rich medium at 30° C. to stationary phase. At the time of harvest, the protease inhibitors phenylmethylsulfonyl fluoride (PMSF) and Pepstatin A were added to a final concentration of 1 mM and 10 uM, respectively. The cells were then removed by centrifugation at 400×g and the medium was filtered through a 0.45 u cellulose acetate filter (Corning Glass Works, Corning, N.Y.). The sterile supernates were stored at 4° C.

EXAMPLE 3

Colony Assay

The presence of human GM-CSF harvested from the yeast cultures in Example 3 was confirmed by assaying the ability of the supernatant to stimulate growth of human bone marrow colonies in agar. For use in the assay, human bone marrow from the iliac crest of healthy donors was collected in a heparinized syringe. The marrow was diluted 1:3 with phosphate buffered saline (PBS) at room temperature and layered onto a solution of 54% Percoll (Pharmacia Fine Chemicals). After centrifugation at 500×g at room temperature for 20 minutes, the interface was collected and washed with 20 volumes of PBS. The suspension was then centrifuged at 250×g for 10 minutes at room temperature. The cells were then resuspended in 10 ml of α-Minimal Essential Medium with nucleotides ("α-Mem", Gibco) for cell counting and viability determination. FCS was then added and the cell suspension stored on ice until the assay was carried out.

In the assay, bone marrow cells as prepared above were added at a final concentration of $1\times10^5$/ml to an incubation medium consisting of: (a) seven parts of a solution containing 28.1% FCS, $0.7\times10^{-4}$M 2-mercaptoethanol, 0.12 mg/ml asparagine, 0.7 mg/ml glutamine, 150 units of penicillin G, 150 units of streptomycin, 1.1×α-MEM with nucleotides, and 2.2×vitamins (Gibco); and, (b) three parts of 1.4% bacto-agar solution (Difco). The cultures were incubated in a humidified atmosphere at 37° C. in the presence of 5% $CO_2$. After seven to fourteen days of culture, the number and types of colonies, whether granulocyte, macrophage or mixed granulocyte-macrophage, were determined. Applicants found that the GM-CSF gene from the pY fGM-2 clones directed synthesis of GM-CSF activity at the high level of $1.25\times10^6$ colony forming units per $10^5$ (CFU-c/ml). This activity level was determined by multiplying by 50 the reciprocal of the dilution giving 50% of the maximum colony number. Applicants have found that the average number of colonies from $1\times10^5$ bone marrow cells was 96±29. The colonies formed at 14 days by the recombinant GM-CSF were well defined and consisted of three types: approximately ⅓ mixed granulocyte-macrophage colonies; approximately ⅓ tight granulocyte colonies, and approximately ⅓ dispersed macrophage colonies.

As a control for the expression system of the present invention, a plasmid identical to pYαfGM-2, but lacking the GM-CSF sequences, was also transformed into yeast strain 79. The culture supernatant from the yeast produced no GM-CSF activity in the bone marrow colony forming assay.

EXAMPLE 4

Purification of Recombinant GM-CSF

The medium from Example 2, containing secreted recombinant GM-CSF, was made 1% in TFA and then filtered through 0.45 u filter (Corning Glass Works, Corning, N.Y.). The medium was then pumped directly into a Vydac C4 reverse phase column (1.0×30 cm stainless steel with 10 u packing or Waters radial compression cartridge [Waters Associate, Milford, Me.] packed with 50 u Vydac C4 packing) with the use of a Milton Roy pump (Lab. Data Control, Riveria Beach, Fla.) at a flow rate of 5 ml/min. Up to 1 liter of medium was applied at a time and the total protein load on the column was found to be generally around 20 mg. The load column was washed with 0.1% TFA to remove nonbound sample components until the absorbance at 214 nm dropped to baseline (preloading) values. Elution of the bound protein was accomplished with a linear gradient of 0-95% acetonitrile in 0.1% TFA (v/v) at a rate of 1% acetonitrile/min. The gradient was formed with a Waters liquid chromatograph consisting of a Model 680 gradient former, 2M-45 pumps and a Model 414 detector monitoring at 214 nm. Peak protein fractions were observed at from 55 to 60% acetonitrile.

The peak fractions containing GM-CSF from the first HPLC procedure were collected and then diluted 1:3 in 0.1% TFA (v/v) in $H_2O$, and then the activity was subjected to re-chromatography and re-elution with the same gradient of TFA and acetonitrile on a Vydac C18 column (3.9 mm×15 cm column, 5 u packing). Peak fractions were observed at from 55 to 60% acetonitrile.

Fractions were analyzed for protein by fluorescamine assay. Also, peak fractions were again analyzed by SDS polyacrylamide gel electrophoresis followed by silver staining. In the electrophoresis process, 20 ul aliquots from the fractions collected during the elution procedure are dried under vacuum after the addition of 2 ml of 10% SDS to each aliquot. The dried residue was dissolved in 40 ul of nonreducing sample buffer composed of 0.0625M Tris (pH 6.8); 2% SDS (w/u); 10% glycerol (v/v); and, 5% 2-mercaptoethanol (v/v). The solution was boiled for 3 min. and then subjected to electrophoresis on 12% polyacrymide gel by the method described by Laemmil, *Nature (London)*, 227:680 (1970). The gel samples for the individual fraction numbers were silver stained by the method described by Oakley et al., *Anal. Biochem.*, 105:361–364 (1980). Essential homogeneity of the GM-CSF was confirmed by the electrophoresis and silver staining which yielded two protein bands corresponding to glycosylated (21,000 daltons) and nonglycosylated (17,000 daltons) species of GM-CSF, FIG. 5. The activity of this homogeneous material, as analyzed with the colony forming assay detailed in Example 3 above, was found to be approximately $1.5 \times 10^7$ CFU-c/ml, with a specific activity of $1.5 \times 10^6$ CFU-c/ug of protein. The pI value was found to be approximately from 5.0 to 5.4.

EXAMPLE 5

Preparation of Labeled Target Cells

Target cells were maintained in RPMI 1640 medium supplemented with 5% at 37° C. in a humidified atmosphere containing 5% $CO_2$. Cytotoxicity assays were performed when the cultured target cells were in their exponential growth phase. Target cells included the human melanoma cell line A375 (ATCC No. CRL 1619), the human liver carcinoma cell line SK-Hep-1 (ATCC No. HTB-52), the human pancreatic carcinoma MIA-PACA-2 (ATCC No. CRL-1420) and the human bladder carcinoma 5637 (ATCC No. HTB-9).

The exponentially growing target cells were radiolabeled with $^{125}$I-IUdR. In the radiolabeling procedure, target cells were incubated at 37° C. for 24 hours in RPMI medium supplemented with 5% FCS medium containing $^{125}$I-IUdR (0.3 uCi/ml; specific activity, 200 mCi/ml; New England Nuclear, Boston, Mass.). The cells were then washed twice to remove unbound radiolabel and then harvested by a 1 min. trypsinization with 0.25% trypsin (Difco Labs, Detroit, Mich.) and 0.02% EDTA. The labeled cells were resuspended in RPMI-1640 medium supplemented with 5% FCS.

EXAMPLE 6

Tumoricidal Activity Assays

In the tumoricidal assay procedure, 200 ul volumes of various concentrations/dilutions of test samples of recombinant GM-CSF, from Example 2, purified natural IFN-γ (Meloy Laboratories, Springfield, Va.), LPS (Difco Labs., Detroit, Mich., *E. coli* LPS-N) and LPS combined with IFN-γ were added to the culture wells containing the plated monocytes. As noted in Example 1, prior to adding the test samples to the monocytes, nonadherent monocyte cells were removed from the culture wells by aspirating with an 18 gauge needle and then the monolayers were rinsed twice with serum-free RPMI-1640. With respect to the GM-CSF, assays were conducted with various dilutions of both supernate produced by yeast containing the GM-CSF plasmid, as prepared in Example 2 above (FIG. 3), and purified recombinant GM-CSF as prepared in Example 5 (FIG. 4). The dilutions of LPS, IFN-γ and LPS together with IFN-γ are also set forth in FIGS. 3 and 4. As a control, assays were conducted with supernates produced by yeast which did not contain the GM-CSF plasmid. After 24 hours of incubation of test samples with resting monocytes, the test samples were aspirated off.

Approximately $10^4$ $^{125}$I-UdR-labeled target cells from Example 5 were added to each of the monocyte wells to obtain an initial target-to-effector (activated monocyte) cell ratio of between 1:10 and 1:20. Also, radiolabeled target cells were plated alone as an additional control group. Because the assay measures lysis of adherent target cells in which cell-to-cell contact between effector and target cells is required, after 24 hours the culture supernatants were aspirated off and fresh RPMI-1640 medium replaced to eliminate potential errors due to cells that did not adhere but were not necessarily killed in the assay. After an additional 48 hours, the monolayers were vigorously rinsed to remove target cells killed by the monocytes. The adherent viable cells remaining in each well were lysed with 50 ul of 0.5M NaOH. The residual counts were collected with a cotton swab and then the radioactivity measured with a γ counter. The percentage of monocyte-mediate cytotoxicity was calculated according to the formula:

$$\text{Percentage of generated cytotoxicity} = 100 - \frac{\text{cpm in target cells cultured with stimulated monocytes}}{\text{cpm in target cells cultured with resting monocytes}} \times 100$$

FIGS. 3 and 4 contain the assay results. As shown in FIG. 3, and as expected, LPS and IFN-γ interferon did activate macrophages to the point where they mediated tumoricidal activity. Also as previously reported, the effectiveness of IFN-γ as a macrophage activator was only significant when added together with a small amount of LPS. As further shown in FIG. 3, supernate produced by yeast containing the GM-CSF plasmid was effective in inducing macrophages to kill tumor cells while control supernate (produced by yeast which did not contain the GM-CSF plasmid) was unsuccessful in inducing macrophage cytotoxicity.

FIG. 4 shows a full course dose titration of purified recombinant GM-CSF. As shown in FIG. 4, even at a dilution of 1:500,000 purified recombinant GM-CSF still had a capacity to activate macrophages to express tumoricidal activity (30 CFU-c/ml), and half-maximal induction of generated specific cytotoxicity occurred at a dilution of the column fraction of approximately 1:1,000,000 (15 CFU-c/ml). As in FIG. 3, appropriate controls of LPS, IFN-γ and IFN-γ plus LPS are also shown in FIG. 4. Unlike with IFN-γ, GM-CSF served as an effective single signal to activate macrophages into tumoricidal activity in the absence of exogenous LPS.

EXAMPLE 7

Tumoricidal Activity Assay-Human Carcinoma Cell Line

The tumoricidal activity assay set forth in Example 6 is also conducted with respect to the human bladder squamous carcinoma SCaBER (ATCC No. HTB 3). These targets cells are radiolabeled in a manner detailed in Example 5. The assay is conducted using the same procedure set forth in Example 6 with the exception that radiolabeled SCaBER target cells are used in place of the A375 target cells.

EXAMPLE 8

Tumoricidal Activity Assay-Human Myeloma

The tumoricidal assay procedure of Examples 6 and 7 is employed in conjunction with the human malignant myeloma SK-MEL-28 (ATCC No. HTB 72). The target cells are radiolabeled as detailed in Example 5. The assay is conducted in the same manner as set forth in Examples 6 and 7 with the exception that SK-MEL-28 cells are employed as target cells.

EXAMPLE 9

Tumoricidal Activity Assay-Human Hepatoma

The tumoricidal activity assay set forth in Example 6 was also conducted with respect to the human liver carcinoma SK-Hep-1 (ATCC No. HTB-52). The target cells were radiolabeled in a manner detailed in Example 5. In the assay, the GM-CSF was employed at a concentration of 10 nanograms per milliliter (ng/ml) of assay volume. Approximately $10^4$ $^{125}$IUdr-labeled target cells were used in each assay to obtain an initial target: effector (activated monocyte) cell ratio of between 1:20 and 1:30. Also, radiolabeled target cells were plated alone as a control. In this assay, the GM-CSF activated monocytes were found on the average to mediate specific cytotoxicity of the tumor cells at a level of about 14%.

EXAMPLE 10

Tumoricidal Activity Assay-Human Pancreatic Carcinoma

The tumoricidal assay procedure of Example 9 was employed in conjunction with the human pancreatic carcinoma cell line MIA PACA-2 (ATCC No. CRL 1420). The target cells were radiolabeled as detailed in Example 5. The assay was conducted in the manner delineated in Example 9, with the exception that the MIA PACA-2 cells were employed as target cells. In this particular assay, the average percentage of generated cytotoxicity was found to be approximately 38%.

EXAMPLE 11

Tumoricidal Activity Assay-Human Bladder Carcinoma

The tumoricidal assay procedure of Example 9 was also employed in conjunction with the human bladder carcinoma cell line 5637 (ATCC No. HTB-9). The target cells were labeled as detailed in Example 5. The assay was conducted in the same manner as set forth in Example 9 with the exception that 5637 cells were employed as target cells. In this particular assay, the percentage of generated cytotoxicity was found to be about 30%. This particular assay and those set forth above illustrate that GM-CSF served as an effective single signal to activate macrophages into tumoricidal activity.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples contained in the foregoing description.

The embodiments of the invention in which an exclusive property or privilege is claimed are defined as follows:

1. A method of priming human cells of macrophage lineage to become tumoricidal comprising the step of introducing into the body of a human having tumor cells from about 1.0 to about $10^6$ μg/kg of a human granculocyte-macrophage colony stimulating factor effective to prime said cells of macrophage lineage in vivo to become tumoricidal.

2. The method of claim 1, wherein the granulocyte-macrophage colony stimulating factor is introduced into the body by a method selected from the group consisting of injection, orally, aerosol inhalation, transdermal or transbuccal absorption or rectal suppository.

3. The method of claim 2, wherein the method of injection is selected from the group consisting of subcutaneous, intramuscular, intraperitoneal, and intravenous injections.

4. The method of claim 1, wherein the granulocyte-macrophage colony stimulating factor is of recombinant origin.

5. The method of claim 4, wherein the granulocyte-macrophage colony stimulating factor is purified to a specific activity of at least about $1.5 \times 10^6$ colony forming units per microgram as determined by bone marrow colony forming assay.

6. The method of claim 4, wherein the granulocyte-macrophage colony stimulating factor is encoded by a nucleic acid sequence comprising nucleic acid No. 14 to nucleic acid No. 394 in FIG. 1.

7. The method according to claim 4, wherein the granulocyte-macrophage colony stimulating factor comprises amino acid residue No. 1 to amino acid residue No. 127 in FIG. 1.

8. A method of treating a tumor in a human subject, comprising
   (a) isolating cells of macrophage lineage selected from the group consisting of macrophages and monocytes from the body of a human donor;
   (b) culturing the cells in the presence of purified recombinant human granulocyte-macrophage colony stimulating factor (GM-CSF) in an amount and for a time sufficient to generate at least about 10 percent specific cytotoxicity, as may be determined by a monocyte- or macrophage-mediated cytotoxicity assay, thereby to provide activated cells; and
   (c) administering the activated cells to the human subject to treat the tumor.

9. A method according to claim 8, wherein the tumor is a carcinoma, melanoma or sarcoma.

10. A method according to claim 9, wherein the carcinoma is a bladder, kidney, squamous cell, lung, liver, breast or colon carcinoma.

11. A method according to claim 8, wherein the donor and subject are the same individual.

12. A method according to claim 11, wherein the cells are cultured in the presence of about 0.01 to 100 nanograms of GM-CSF per $2 \times 10^5$ cells of macrophage lineage.

13. A method according to claim 12, wherein the cells are peripheral blood monocytes.

14. A method according to claim 13, wherein the cells are cultured in the presence of such quantity for at least 24 hours.

15. A method according to claim 8, wherein the GM-CSF is purified to a specific activity of at least about $1.5 \times 10^6$ colony forming units per microgram of protein as determined by the bone marrow colony forming assay.

16. A method according to claim 15, wherein the GM-CSF comprises amino acid residue No. 1 to amino acid residue No. 127 in FIG. 1.

17. A method according to claim 16, wherein the GM-CSF is prepared by expression of a recombinant plasmid in a yeast host and purified to essential homogeneity by reverse-phase high-performance liquid chromatography.

18. A method of priming human cells of macrophage lineage selected from the group consisting of macrophages and monocytes to become tumoricidal comprising:
(a) determining a dosage of purified recombinant human GM-CSF from about 1.0 to $1 \times 10^6$ μg/kg/day, wherein said dosage is effective to prime said cells of macrophage lineage when administered parenterally to the subject;
(b) formulating said dosage in single or multiple doses for parenteral administration to the subject; and
(c) administering said single or multiple doses by subcutaneous, intramuscular, intraperitoneal or intravenous injection, in said dosage effective to prime said cells in vivo to become tumoricidal.

19. A method according to claim 18, wherein a therapeutically effective dosage or dosages is determined by intitiating treatment at a lower level of said dosage range and increasing dosage until a therapeutic effect is achieved.

20. A method according to claim 18, wherein the tumor is a carcinoma, melanoma or sarcoma.

21. A method according to claim 20, wherein the carcinoma is a bladder, kidney, squamous cell, lung, liver, breast or colon carcinoma.

22. A method according to claim 21, wherein the cells are peripheral blood monocytes.

23. A method according to claim 18, wherein the GM-CSF is purified to a specific activity of at least about $1.5 \times 10^6$ colony forming units per microgram of protein as determined by the bone marrow colony forming assay.

24. A method according to claim 23, wherein the GM-CSF comprises amino acid residue No. 1 to amino acid residue No. 127 in FIG. 1.

25. A method according to claim 24, wherein the GM-CSF is prepared by expression of a recombinant plasmid in a yeast host and purified to essential homogeneity by reverse-phase high-performance liquid chromatography.

26. A method according to claim 18, further comprising the step of measuring the effect of parenteral GM-CSF administration by a monocyte- or macrophage-mediated cytotoxicity assay or by condition of the subject.

* * * * *

UNITED STATES PATENT AND TRADEMARK OFFICE
CERTIFICATE OF CORRECTION

PATENT NO. : 5,078,996

DATED : January 7, 1992

INVENTOR(S) : Paul J. Conlon, III and Kenneth H. Grabstein

It is certified that error appears in the above-identified patent and that said Letters Patent is hereby corrected as shown below:

Column 1, line 44, the word "distint" should read -- distinct --.

Column 8, line 27, the word "absorption" should read -- adsorption --.

Column 16, line 5, the word "absorption" should read -- adsorption --.

Column 16, line 16, after the word "microgram," please add -- of protein --.

Column 16, line 22, please delete "according to" and add -- of --.

Signed and Sealed this

Twenty-seventh Day of April, 1993

Attest:

MICHAEL K. KIRK

*Attesting Officer*    Acting Commissioner of Patents and Trademarks